(12) United States Patent
Lamansky et al.

(10) Patent No.: US 6,911,271 B1
(45) Date of Patent: Jun. 28, 2005

(54) ORGANOMETALLIC PLATINUM COMPLEXES FOR PHOSPHORESCENCE BASED ORGANIC LIGHT EMITTING DEVICES

(75) Inventors: Sergey Lamansky, Camarillo, CA (US); Mark E. Thompson, Anaheim, CA (US)

(73) Assignee: The University of Southern California, Los Angeles, CA (US)

( * ) Notice: Subject to any disclaimer, the term of this patent is extended or adjusted under 35 U.S.C. 154(b) by 112 days.

(21) Appl. No.: 09/637,766

(22) Filed: Aug. 11, 2000

(51) Int. Cl.$^7$ .......................... H05B 33/14; C09K 11/06
(52) U.S. Cl. ...................... 428/690; 428/917; 313/504; 252/301.16; 546/2; 546/4; 546/10
(58) Field of Search ................................ 428/690, 917; 313/504, 506; 257/40, 102, 103; 252/301.16; 546/2, 4, 10, 101, 281.1, 326, 346

(56) References Cited

U.S. PATENT DOCUMENTS

| | | | | |
|---|---|---|---|---|
| 5,779,937 | A | * 7/1998 | Sano et al. | 252/301.16 |
| 6,303,238 | B1 | * 10/2001 | Thompson et al. | 428/690 |
| 6,310,360 | B1 | * 10/2001 | Forrest et al. | 257/40 |
| 6,656,608 | B1 | 12/2003 | Kita et al. | 428/690 |
| 6,670,645 | B2 | 12/2003 | Grushin et al. | 257/98 |
| 2002/0034656 | A1 | 3/2002 | Thompson et al. | 428/690 |

FOREIGN PATENT DOCUMENTS

| | | |
|---|---|---|
| EP | 0 579 151 A2 | * 1/1994 |
| EP | 0 757 088 A2 | * 2/1997 |

OTHER PUBLICATIONS

B. N. Cockburn et al., "Reactivity of Co-ordinated Ligands . . . ", Journal of the Chemical Society. Dalton Transactions, vol. 4, pp. 404–410 (1973), no month.*
Gaetano DiMarco et al., "Luminescent Mononuclear and Dinuclear Iridium(III) Cyclometalated Complexes . . . ", Anal. Chem., vol. 70, pp. 5019–5023, Dec. 1, 1998.*
Mauro Maestri et al., "Photochemistry and Luminescence of Cyclometallated Complexes", in Advances in Photochemistry, vol. 17, edited by David Volman et al., 1992, pp. 1–68, no month.*
Y. Ma, et al., "Electroluminescence from triplet metal–ligand charge–transfer excited state of transition metal complexes", Synthetic Metals 94 (1998), pp. 245–248.
H.F. Wittmann, et al., "Optical specroscopy of platinum and palladium containing poly–ynes", J. Chem. Phys., vol. 101, No. 4, pp. 2693–2698, Aug. 15, 1994.

M.A. Baldo, et al., "Phosphorescent materials for application to organic light emitting devices", Pure Appl. Chem., vol. 71, No. 11, pp. 2095–2106, 1999.
G. DiMarco, et al., "A Luminescent Iridium(III) Cyclometallated Complex Immobilized in a Polymeric Matrix as a Solid–State Oxygen Sensor", Advanced Materials, vol. 8, pp. 576–580, Jul. 1996.
J.N. Demas, et al., Design and Applications of Highly Luminescent Transition Metal complexes, Analytical Chemistry, vol. 63, No. 17, pp. 829–837, Sep. 1, 1991.
K. Vinodgopal, et al., "Photochemistry of Ru(bpy)2(dcbpy)2+ on Al2O3 and TiO2 Surfaces. An Insight into the Mechanism of Photosensitization", J. Phys. Chem. 1995, 99, pp. 10883–10889.
R. Holmlin et al., "Os(phen)2dppz2+ in Photoinduced DNA–Mediated Electron Transfer Reactions", J. Am. Chem. Soc. 1996, 118, pp. 5236–5244.
Lamansky et al., *Optical Properties of Pt(II) Cyclometalated Complexes in Polymer Matrices, Preparation and Potential Uses in OLEDs*, Abstracts of Papers, Part 1, 217$^{th}$ ACS National Meeting, Anaheim, CA (Mar. 21–25, 1999).
Chemistry.ORG, The Website of the American Chemical Society, Internet Schedule of 217$^{th}$ ACS National Meeting, (Mar. 21–25, 1999); printed on Jul. 22, 2003.
Y. Kunugi, et al., "A Vapochromic LED", *J. Am. Chem. Soc.*, vol. 120, No. 3, pp. 589–590, 1998, no month.
M. A. Baldo, et al., "Highly efficient phosphorescent emission from organic electroluminescent devices," Nature, Sep. 1998, vol. 395, pp. 151–154.
G.W.V. Cave et al., "C–H Activation Induced by Water. Monocyclometalated to Dicyclometalated: C$^\wedge$N$^\wedge$C Tridentate Platinum Complexes", Organometallics 2000, vol. 19, No. 7, pp. 1355–1364, no month.
M. A. Baldo, et al., "High–efficiency fluorescent organic light–emitting devices using a phosphorescent sensitizer", Nature, vol. 403, pp. 750–753, Feb. 17, 2000.
M.A. Baldo, et al., "Very high–efficiency green organic light–emitting devices based on electrophosphorescence", Applied Physics Letters, vol. 75, No. 1, pp. 4–6, Jul. 5, 1999.
Von Zelewsky, et al., "Tailor Made Coordination Compounds for Photochemical purposes", Coordination Chemistry Reviews, 132 (1994) pp. 75–85, no month.

* cited by examiner

*Primary Examiner*—Marie Yamnitzky
(74) *Attorney, Agent, or Firm*—Kenyon & Kenyon

(57) ABSTRACT

A device for producing electroluminescence comprising an organic light emitting device including an emissive layer comprising an organometallic compound comprised of a metal bound to a single carbon-coordination ligand, with the single carbon-coordination ligand being a mono-anionic carbon-coordination ligand.

15 Claims, 8 Drawing Sheets

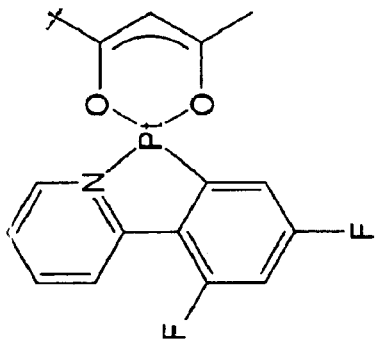
Fig. 1d (4,6-F₂ppy)Pt(acac)
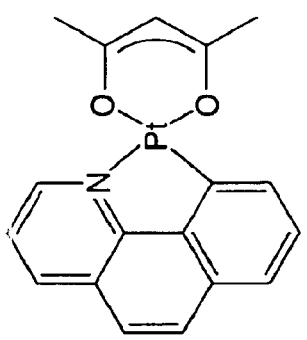
Fig. 1c (bzq)Pt(acac)
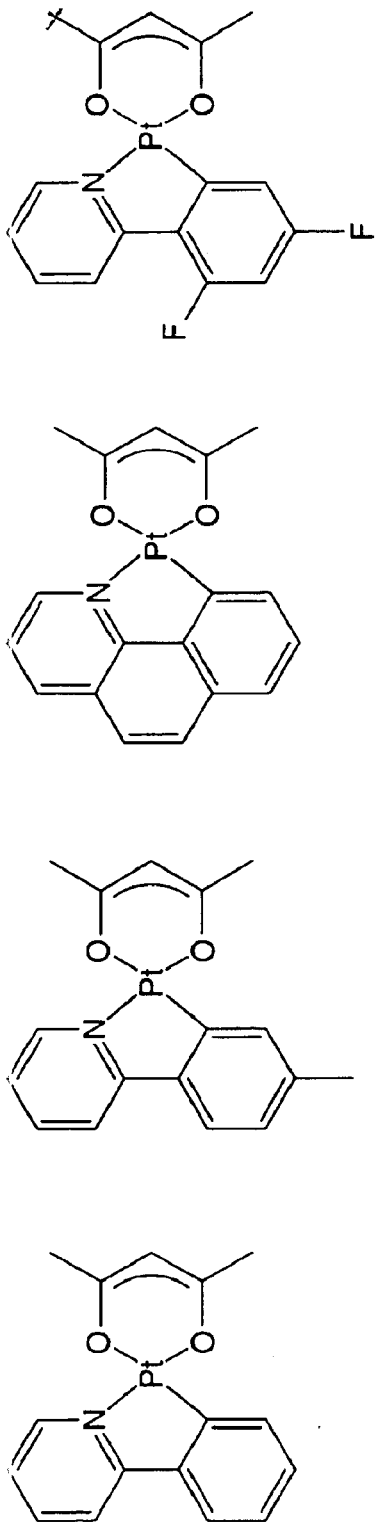
Fig. 1b (tpy)Pt(acac)
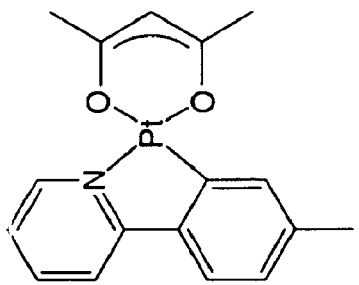
Fig. 1a (ppy)Pt(acac)
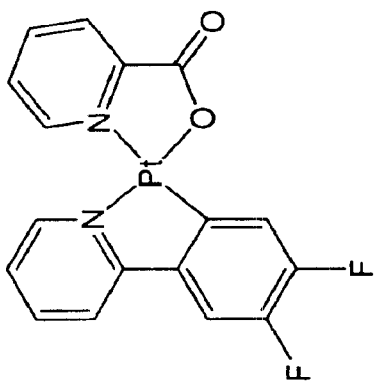
Fig. 1g (4,5-F₂ppy)Pt(pico)
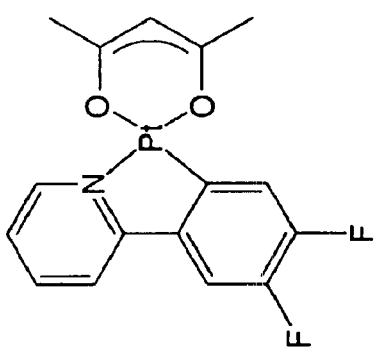
Fig. 1f (4,5-F₂ppy)Pt(acac)
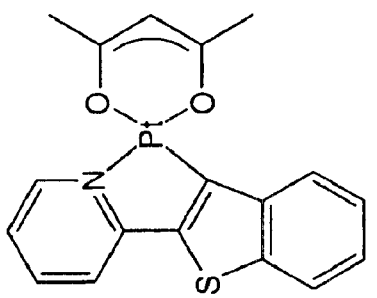
Fig. 1e (btp)Pt(acac)

US 6,911,271 B1

ORGANOMETALLIC PLATINUM COMPLEXES FOR PHOSPHORESCENCE BASED ORGANIC LIGHT EMITTING DEVICES

GOVERNMENTS RIGHTS

This invention was made with Government support under Contract No. F33615-94-1-1414 awarded by DARPA. The government has certain rights in this invention.

RESEARCH AGREEMENTS

The claimed invention was made by, on behalf of, and/or in connection with one or more of the following parties to a joint university-corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention is directed to phosphorescence based organic light emitting devices that have improved electroluminescent characteristics.

BACKGROUND OF THE INVENTION

The technology of organic light emitting diodes (OLEDs) is undergoing rapid development. OLEDs originally utilized the electroluminescence produced from electrically excited molecules that emitted light from their singlet states. Such radiative emission from a singlet excited state is referred to as fluorescence. More recent work has demonstrated that higher power efficiency OLEDs can be made using molecules that emit light from their triplet state, defined as phosphorescence.

Such electrophosphorescence makes it possible for phosphorescent OLEDs to have substantially higher quantum efficiencies than are possible for OLEDs that only produce fluorescence. This is based on the understanding that the excitons created in an OLED are produced, according to simple statistical arguments as well as experimental measurements, approximately 75% as triplet excitons and 25% as singlet excitons. The triplet excitons more readily transfer their energy to triplet excited states that can produce phosphorescence whereas the singlet excitons typically transfer their energy to singlet excited states that can produce fluorescence. Since the lowest emissive singlet excited state of an organic molecule is typically at a slightly higher energy than the lowest triplet excited state, the singlet excited state may relax, by an intersystem crossing process, to the emissive triplet excited state. This means that all the exciton excitation energy may be converted into triplet state excitation energy, which then becomes available as phosphorescent emission. Thus, electrophosphorescent OLEDs have a theoretical quantum efficiency of 100%, since all the exciton excitation energy can become available as electrophosphorescence.

As a consequence, since the discovery that phosphorescent materials could be used in an OLED, Baldo et al., "Highly Efficient Phosphorescent Emission from Organic Electroluminescent Devices" *Nature*, vol. 395, 151–154, 1998, there is now much interest in finding more efficient electrophosphorescent materials.

Typically phosphorescent emission from organic molecules is less common than fluorescent emission. However, phosphorescence can be observed from organic molecules under an appropriate set of conditions. Organic molecules coordinated to lanthanide elements often phosphoresce from excited states localized on the lanthanide metal. The europium diketonate complexes illustrate one group of these types of species. Organic phosphorescence is also often observed in molecules containing heteroatoms with unshared pairs of electrons at very low temperatures. Benzophenone and 2,2'-bipyridine are such molecules. Phosphorescence can be enhanced over fluorescence by confining, preferably through bonding, the organic molecule in close proximity to an atom of high atomic number. This phenomenon, called the heavy atom effect, is created by a mechanism known as spin-orbit coupling. A related phosphorescent transition is a metal-to-ligand charge transfer (MLCT) that is observed in molecules such as tris(2-phenylpyridine)iridium(III).

However, molecules that phosphoresce from MLCT states typically emit light that is of lower energy than that observed from the unbound organic ligand. This lowering of emission energy makes it difficult to develop organic molecules that phosphoresce in the technologically useful blue and green colors of the visible spectrum where the unperturbed phosphorescence typically occurs.

It would be desirable if more efficient electrophosphorescent materials could be found, particularly materials that produce their emission in the blue region of the spectrum.

SUMMARY OF THE INVENTION

The present invention is directed to organic light emitting devices, and methods of fabricating the same, that involve using emissive organometallic compounds that produce improved electroluminescence.

Specific embodiments of the present invention are directed to OLEDs using emissive organometallic compounds that produce improved electrophosphorescence in the blue region of the visible spectrum.

The present invention is directed, in addition, to a method of selecting organometallic compounds that have improved electroluminescent properties, for example, in the blue region of the visible spectrum.

The organometallic compounds of the present invention include, in particular, compounds having a metal atom bound to a single carbon-coordination ligand, wherein the carbon-coordination ligand is a mono-anionic carbon-coordination ligand.

A carbon-coordination ligand is a ligand that is bound to the metal atom via a carbon metal bond. In view of what one skilled in the art might view as a strict definition of organometallic compounds, such as described in Inorganic Chemistry, by Gary L. Miessler and Donald A. Tarr, 2nd edition, Prentice Hall, 1999, the compounds of the present invention are referred to herein as organometallic compounds since these compounds include a metal carbon bond.

The preferred metals of the present invention are metals that can provide strong spin-orbit orbit coupling of the metal atoms with the carbon-coordination ligand. Such metals include, in particular, the heavy metals having an atomic number of at least 72. Particularly preferred metals include Pt, Ir and Au, with the most preferred being Pt.

The organometallic compounds of the present invention have a single carbon-coordination ligand wherein the single carbon-coordination ligand is a mono-anionic ligand. In particular, the metal atom is bound to only one carbon atom of the carbon-coordination ligand. Thus, while the organometallic compounds that are used in the OLEDs of the present invention may typically include more than one ligand, only one ligand is a carbon coordination ligand. Thus, the organometallic compounds of the present invention include only one carbon-metal bond.

The carbon-coordination ligand is preferably selected from those ligands that exhibit strong charge transfer absorption characteristics, for example, a molar absorptivity of at least 1,000 L/mole-cm, preferably, at least about 2,000–4,000 L/mole-cm. Such absorption bands involve transfer of electrons from molecular orbitals that are primarily ligand in character to orbitals that are primarily metal in character or, alternatively, from orbitals that are primarily metal in character to molecular orbitals that are primarily ligand in character. Miessler and Tarr. Such an excitation mechanism results in a charge transfer transition that may be designated as a ligand-to-metal charge transfer (LMCT) or as a metal-to-ligand charge transfer (MLCT), respectively. The former may be characterized as a partial reduction of the metal atom and the latter as a partial oxidation of the metal atom.

Selection of a carbon-coordination ligand to give a high molar absorptivity of the organometallic compound results in an organometallic compound that is capable of providing highly efficient electroluminescence when used in an OLED. However, rather than functioning as strongly absorbing species in the OLED, such organometallic compounds have highly emissive excited states that are produced when a voltage is applied across the OLED. The high molar absorptivities of such ligands may be used to select ligands that produce highly efficient electroluminescence in an OLED. Such ligands may be selected to have empty pi-symmetry orbitals on the ligands that become acceptor orbitals upon absorption of light.

In the preferred embodiments of the present invention, the ligand is selected, in particular, so as to give a strong metal-to-ligand charge transfer (MLCT) absorption band. Such ligands are selected to have empty anti-bonding $\pi^*$ orbitals on the ligands that become acceptor orbitals upon absorption of light. As representative embodiments of the present invention, the carbon-coordination ligand may be selected from the class of materials such as described, for example, in Comprehensive Coordination Chemistry, Vols. 1–7, G. Wilkinson, Ed., Pergamon Press, 1987.

In addition to being bound to a single mono-anionic carbon-coordination ligand, the metal atom of the organometallic compounds of the present invention is also bound to one or more additional ligands, each of which are all non-carbon-coordination ligands. A non-carbon-coordination ligand is one that does not form any metal-carbon bonds with the metal atom of the organometallic compound. For the preferred embodiments of the present invention for which a metal to ligand charge transfer complex (MLCT) is employed, the non-carbon-coordination ligands are preferably ligands having a strong electrophilic character such that the ligands draw electrons away from the metal atom. Representative non-carbon-coordination ligands may also be selected, for example, from Comprehensive Coordination Chemistry, Vols. 1–7, G. Wilkinson, Ed., Pergamon Press, 1987.

Without intending to be limited to the theory of how the present invention works, it is believed that the improved electroluminescent properties that are observed for the OLEDs of the present invention may be attributed to a combination of factors. For example, it is believed that selection of heavy metals that are capable of forming metal-to-ligand charge transfer (MLCT) states with carbon-coordination ligands that have empty $\pi^*$ orbitals, such phosphorescent materials produce highly efficient electrophosphorescent OLEDs. The electroluminescence from representative organometallic compounds of the present invention shows a vibronic fine structure that indicates that the emission is from an excited state that has a wave function represented by a mixture of the MLCT state of the organometallic compound and the excited triplet state of the carbon-coordination ligand. Since the radiative emission is from a triplet excited state, the emission is referred to as phosphorescence.

It is further believed a higher energy radiative emission may be achieved by including electron-withdrawing groups on the carbon-coordination ligand and/or by selecting the non-carbon-coordination ligand to have a strong electron withdrawing character. Without being limited to the precise theory of how the higher energy radiative emissive may be achieved, it is believed that the electron-withdrawing groups tend to remove electron density from the highest occupied molecular orbitals (HOMO) that include the ligand and the metal atom, thus altering the relative energy levels of the ground state and the excited state such that the overall MLCT transition energy from the ground state to the excited state increases. The preferred organometallic compounds of the present invention include, thus, strong electronwithdrawing groups on the carbon-coordination ligand and/or non-carbon-coordination ligands having a strong electron-withdrawing character.

Another aspect of the present invention relates to the discovery that OLEDs incorporating emissive organometallic compounds having a single mono-anionic carbon-coordination ligand have substantially higher external quantum efficiencies than compound with bis-substituted carbon-coordination ligands. For example, the compound having the chemical structure [(ppy)Pt(acac)] was found to produce strong photophosphorescence at room temperature. In contrast, a compound having the structure [Pt(ppy)$_2$] was found not to produce any visible photophosphorescence at room temperature.

BRIEF DESCRIPTION OF THE DRAWINGS

FIGS. 1(a)–1(c) shows the chemical structures of representative organometallic compounds described herein.

DETAILED DESCRIPTION OF THE INVENTION

Figure 2:
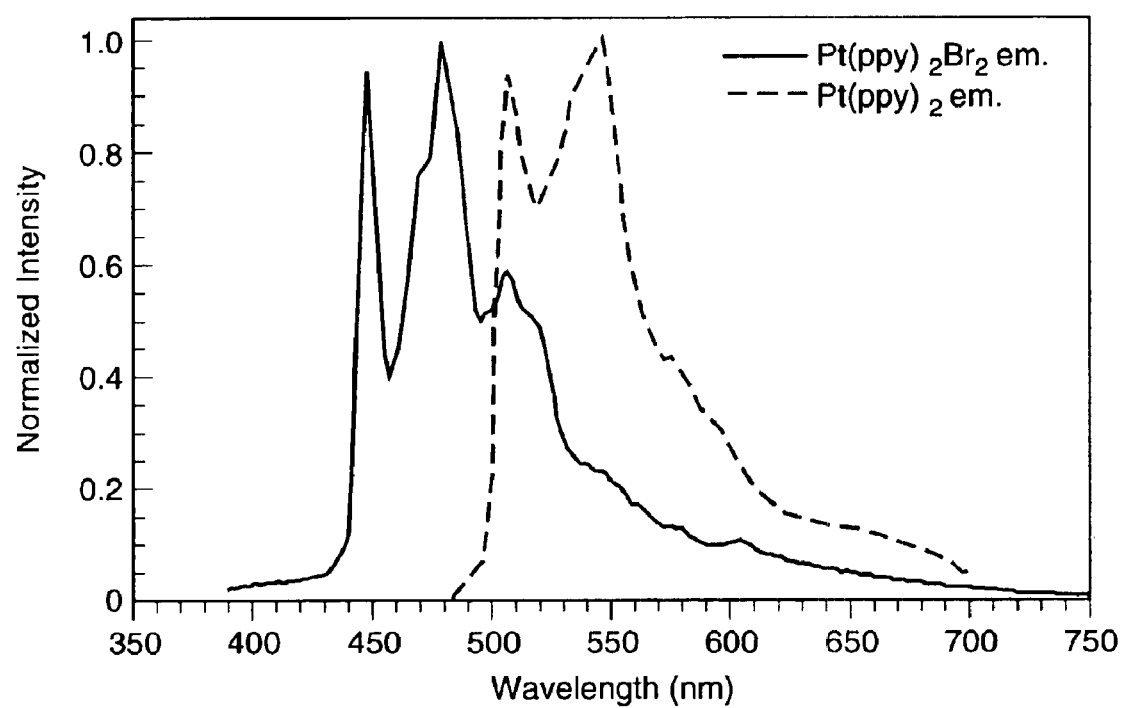
FIG. 2 shows the emission spectrum of both Pt(Ppy)$_2$ and Pt(ppy)$_2$Br$_2$. The former gives green emission, partly from MLCT transitions, and the latter gives blue emission, predominantly from a triplet $\pi$-$\pi^*$ transition. The structure observed for the Pt(ppy)$_2$Br$_2$ spectrum is consistent with ligand-centered emission. The luminescent lifetimes for the two complexes are 4 and 150 microseconds.
Figure 3:
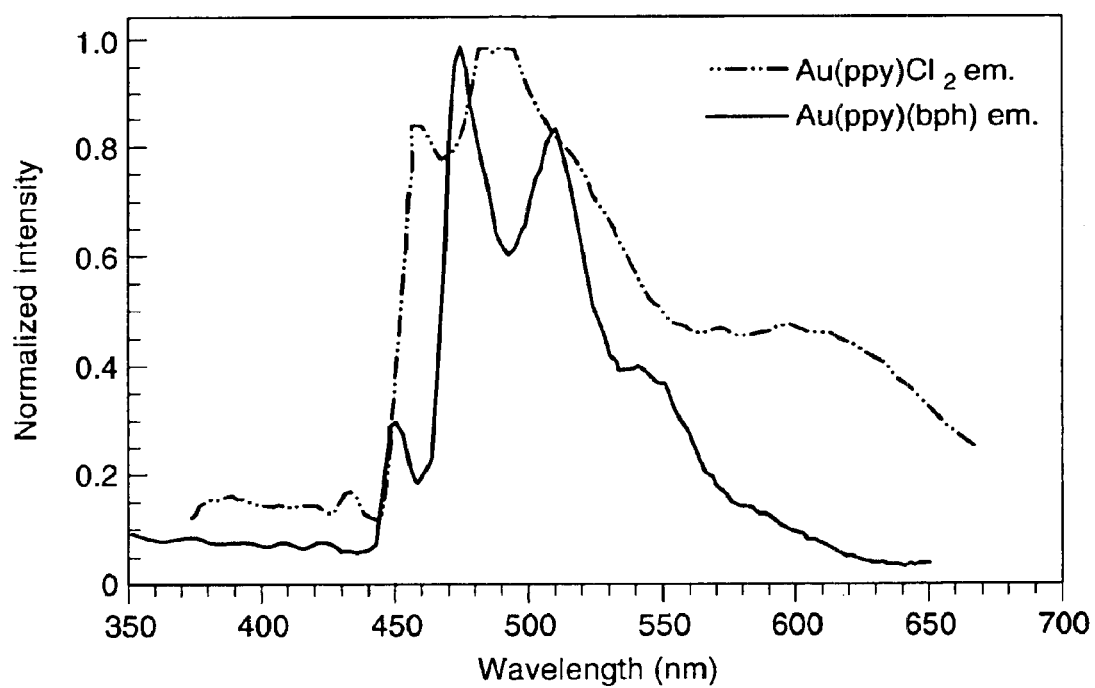
FIG. 3 is a plot showing the emission spectra of (ppy) AuCl$_2$ and (ppy)Au(2,2'-biphenylene). Both emit from ligand triplet $\pi$-$\pi^*$ transitions.

The present disclosure is aimed at a new class of platinum complexes, which give efficient phosphorescence. The representative complexes have a single organometallic ligand (cyclometallated) and a bidentate coordination ligand (such as acetylacetonate). Several examples of these complexes are given below along with their spectra. The emission spectra from these complexes show vibronic fine structure, consistent with strong ligand π-π* character in the phosphorescent transition. Strong ligand π-π* character is also consistent with the fact that the emission energy is strongly dependent on the identity of the ligand, as shown in the spectra shown below. Emission from these complexes results from a mixture of metal to ligand charge transfer (MLCT) and ligand based transitions. The MLCT is critical to enhance the efficiency of intersystem crossing and phosphorescence. The emission is dominated by the cyclometallated ligand and the MLCT between the Pt ion and that ligand. The emission spectrum is only slightly affected by changing the acetylacetonate ligand (acac) to a picolinic acid (pico), as shown for the (ppy)PtX complexes below. This minor shift most likely occurs due to a shift in the Pt based HOMO level by the pico ligand, leading to a red shift in the MLCT and a corresponding red shift in the emission spectrum.

One of these complexes, i.e. (2-(4,5-F$_2$-phenyl)pyridinato)Pt(acetylacetonate), was used as a phosphorescent dopant in a polymer OLED and gave an emission spectrum identical to the photoluminescence spectrum and an external quantum efficiency of 1.3%.

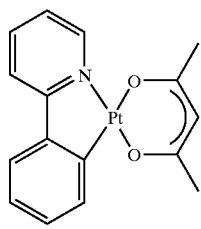

(ppy)Pt(acac)

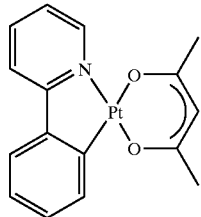

(tpy)Pt(acac)

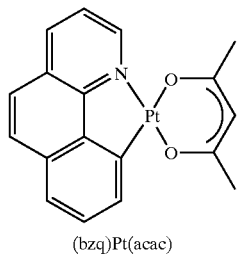

(bzq)Pt(acac)

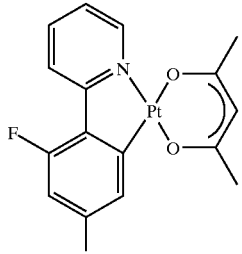

(4,6-F$_2$ppy)Pt(acac)

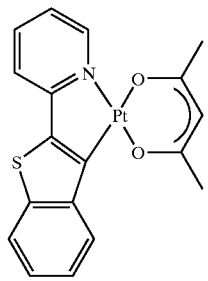

(btp)Pt(acac)

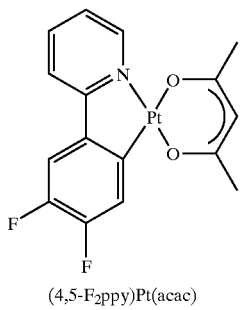

(4,5-F$_2$ppy)Pt(acac)

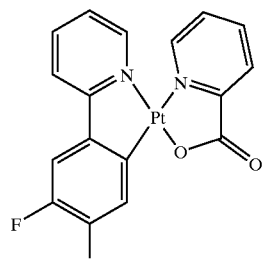

(4,5-F$_2$ppy)(Pt(pico)

As representative electrophosphorescent compounds of the present invention, the carbon-coordination ligand forms a cyclometallated ring that includes the organometallic carbon-metal bond and a dative bond between the metal atom and a nitrogen, sulfur or oxygen group, for example, Pt(II)-(2-phenylpyridinato-N, $C^2$)(acetyl acetonate), herein referred to as Pt(ppy)(acac) or (ppy)Pt(acac). The carbon atom that is bound to the metal may be present as part of a substituted or unsubstituted, saturated hydrocarbon; a substituted or unsubstituted, aromatic system, for example, phenylene or naphthalene compounds; or a substituted or unsubstituted heterocyclic system, which might include, for example, substituted or unsubstituted thiophenes, furans, pyridines and pyrroles. The group in the cyclometallated ring that forms a dative bond with the metal atom may be independently selected also to include a substituted or unsubstituted, saturated hydrocarbon; a substituted or unsubstituted, aromatic system, for example, phenylene or naphthalene compounds; or a substituted or unsubstituted heterocyclic system, which might include, for example, thiophenes, furans, pyridines and pyrroles.

EXAMPLES OF THE INVENTION

All procedures involving $K_2PtCl_4$ or any other Pt species were carried out in inert gas atmosphere in spite of the air stability of the compounds, the main concern being their oxidative stability and stability of intermediate complexes at high temperatures used in the reactions. NMR spectra were recorded on Bruker AMX 360 MHz or 500 MHz instruments unless specified otherwise. Solid probe MS spectra were taken with Hewlett Packard GC/MS instrument with electron impact ionization and model 5873 mass sensitive detector. High resolution mass spectrometry was done at Frick Chem Laboratories at Princeton University. Elemental analysis data was recorded at the Microanalysis Laboratory at the University of Illinois, Urbana-Champaign.

Pt(II) $\mu$-chlorobridged dimers of the structure [Pt(C—N)($\mu$-Cl)$_2$Pt(C—N)] containing cyclometalated carbon, nitrogen ligands (C,N) used in the study were prepared according to Cave G. W. V., Fanizzi F. P., Deeth R. J., Errington W., Rourke J. P., Organometallics 2000, 19, 1355.

Figure 4:
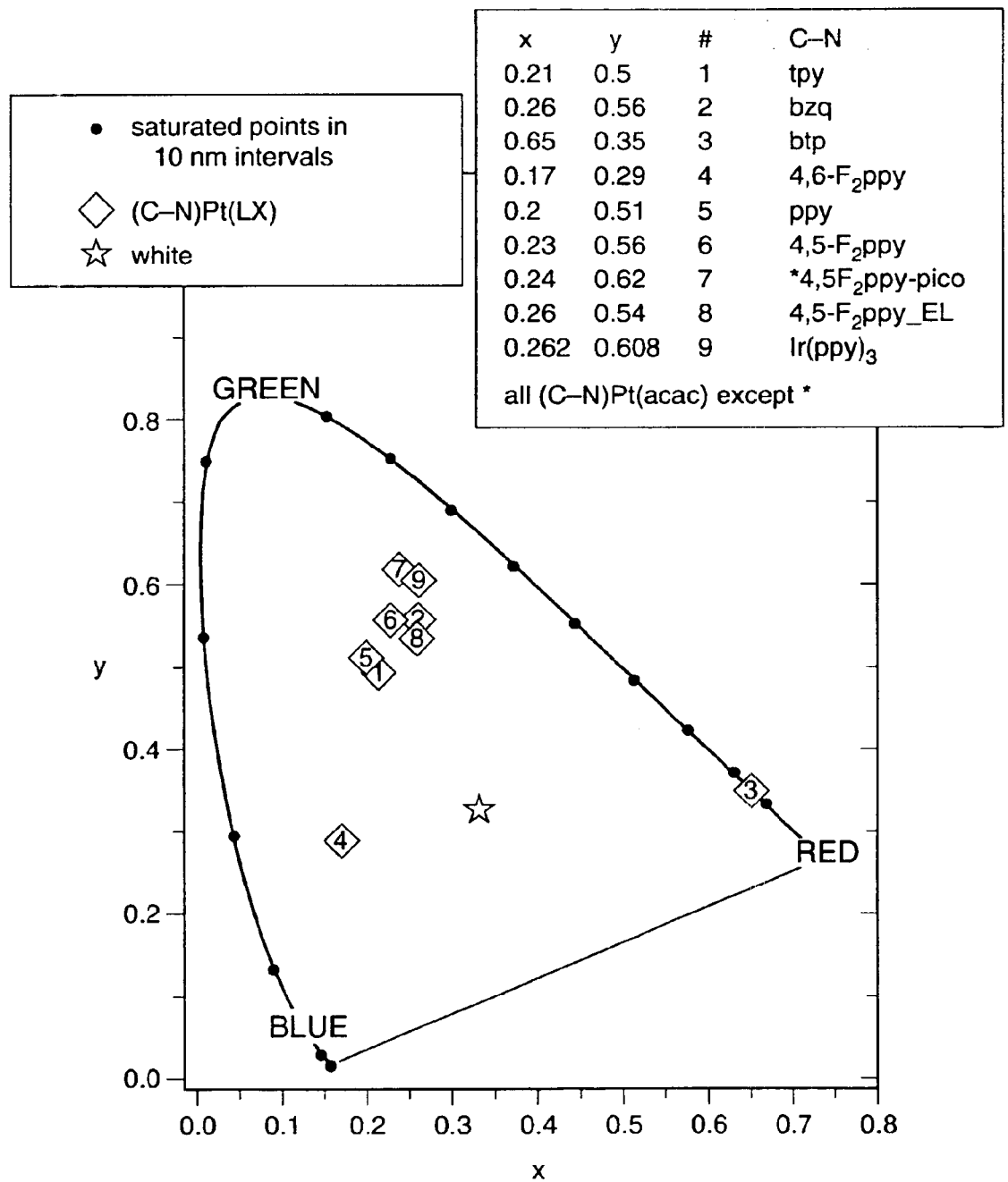
FIG. 4 is a CIE diagram providing the coordinates of (C—N)Pt(acac) complexes. All coordinates are based on solution photoluminescent measurements except for 4,5-F$_2$ ppy-EL, which corresponds to the electroluminescent spectrum. The Ir(ppy)$_3$ is an electroluminescent spectrum as well.
Figure 5:
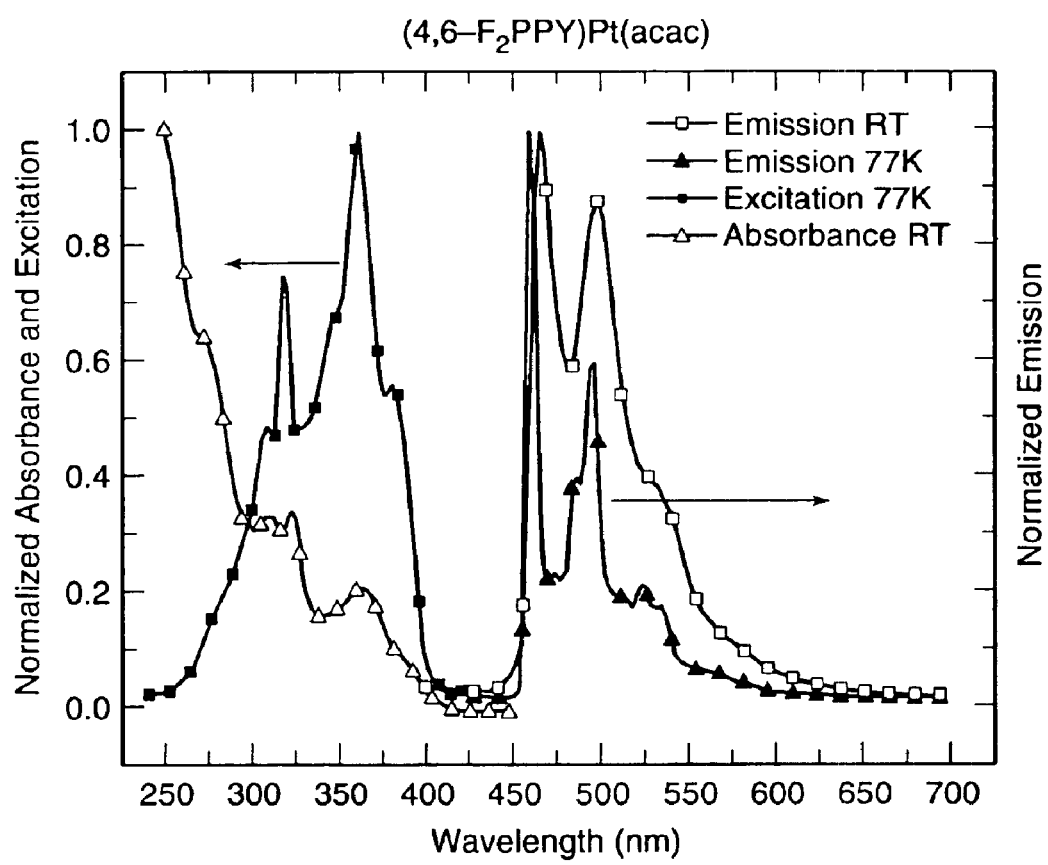
FIG. 5 is a plot depicting the photoluminescent emission spectra of (4,6-F$_2$ ppy)Pt(acac) at room temperature (RT) and at 77 K. Also shown are the excitation spectra taken at 77 K and the absorbance spectra taken at room temperature for the same complex.
Figure 6:
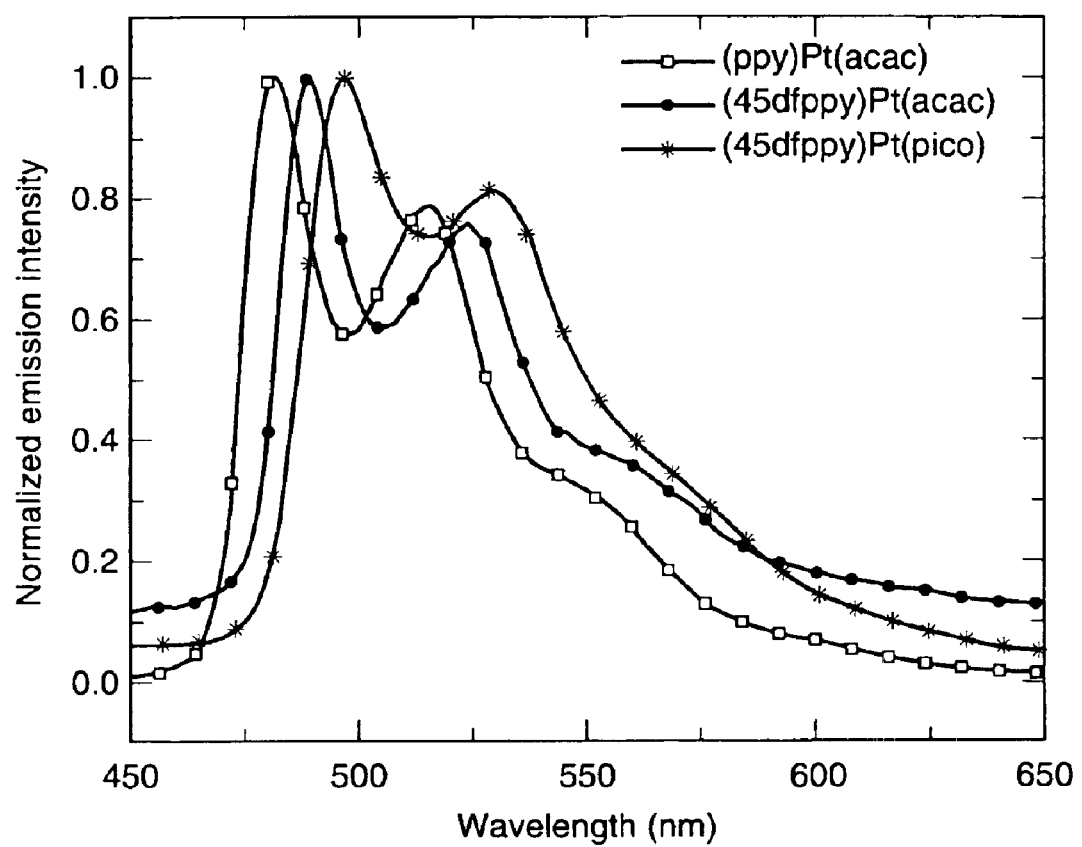
FIG. 6 illustrates the normalized photoluminescent emission spectra of (ppy)Pt(acac), (4,5 dfppy)Pt(acac), and (4,5 dfppy)Pt(pico).
Figure 7:
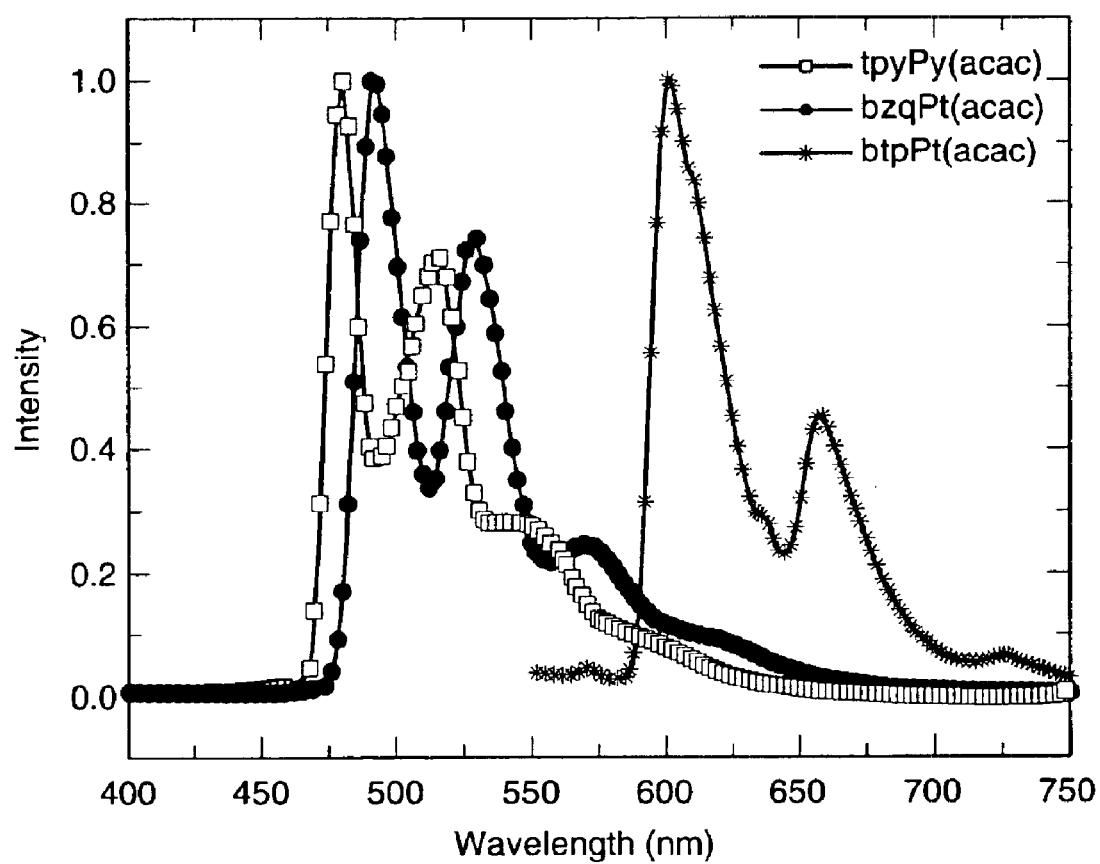
FIG. 7 illustrates the normalized photoluminescent emission spectra of typPy(acac), bzqPt(acac), and btpPt(acac).
Figure 8:
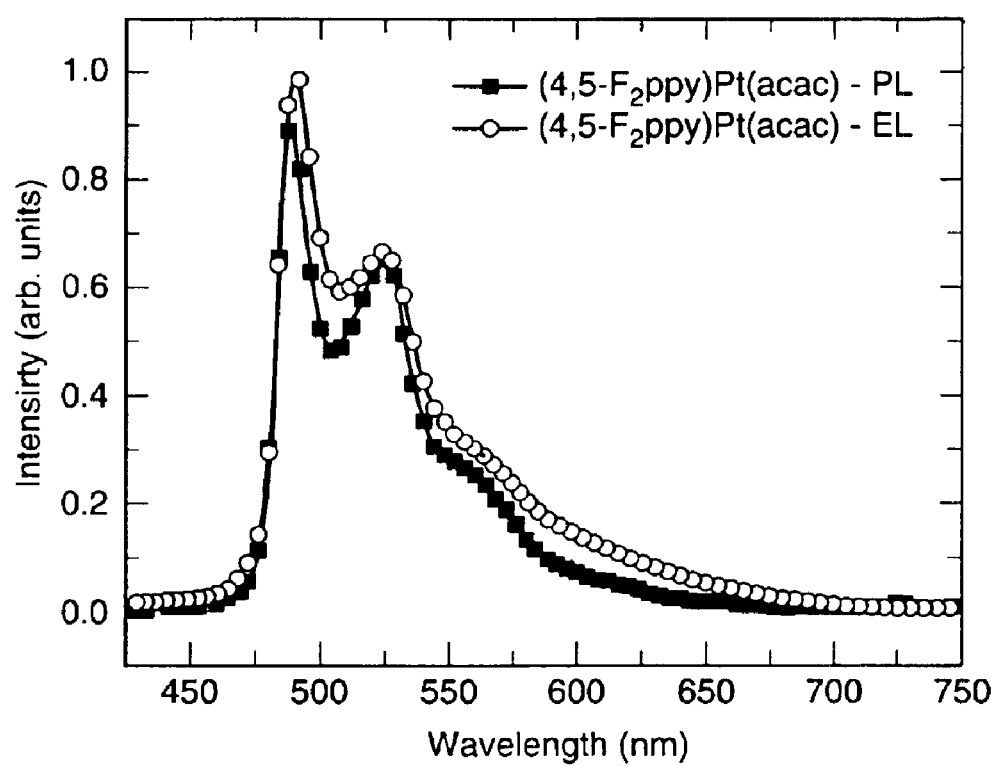
FIG. 8 illustrates the normalized electroluminescent emission spectra for OLEDs prepared with (2-(4,5-F$_2$phenyl)pyridinato)platinum(acetyl acetonate). The OLEDs had a ITO/PVK-PBD-dopant/Alq$_3$/Mg-Ag layer structure. The PVK layer was deposited as a single, homogeneous layer by spin coating. PVK=polyvinylcarbaozole and PBD=(4-biphenyl)(4-tertbutyl)oxidiazole. The Alq$_3$ and Mg-Ag layers were deposited by thermal evaporation. The OLED had an external efficiency of 1.3% and a turn on voltage of 5 Volts. The spectra of the EL output and as well as the PL signal are shown.

Platinum(II) (2-phenylpyridinato-N$C^{2'}$) (acetyl acetonate) [Pt(ppy)(acac)]. 100 mg of Pt(ppy)($\mu$-Cl)$_2$Pt(ppy) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright yellow-green solid (36% yield). $^1$H NMR (360 MHz, acetone-d$_6$), ppm: 9.00 (d, 1H, J 5.8 Hz), 8.02 (dt, 1H, J 1.6, 7.4 Hz), 7.89 (d, 1H, J 7.9H), 7.57 (dd, 1H, J 1.6, 7.4 Hz), 7.51 (dd, 1H, J 1.6, 7.9 Hz), 7.32 (dt, 1H, J 1.6, 6.8 Hz), 7.11 (dt, 1H, J 1.6, 7.9 Hz), 7.04 (dt, 1H, J 1.6, 7.4 Hz), 5.55 (s, 1H), 1.96 (s, 3H), 1.95 (s, 3H). See FIG. 4, compound number 5. See also FIG. 1(a).

Platinum(II) (2-(p-tolyl)pyridinato-N, $C^{2'}$) (acetyl acetonate) [Pt(tpy)(acac)]. 100 mg of Pt(tpy)($\mu$-Cl)$_2$Pt(tpy) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright yellow-green solid (42% yield). $^1$H NMR (360 MHz, CDCl$_3$), ppm: 8.94 (d, 1H, J 5.9 Hz), 7.74 (t, 1H, J 6.8 Hz), 7.53 (d, 1H, J 7.8 Hz), 7.39 (s, 1H), 7.30 (d, 1H, J 7.8 Hz), 7.04 (t, 1H, J 6.8 Hz), 6.88 (d, 1H, J 7.8 Hz), 5.45 (s, 1H), 2.00 (s, 3H), 1.98 (s, 3H), 1.95 (s, 3H). See FIG. 4, compound number 1. See also FIG. 1(b).

Platinum(II) (7,8-benzoqionolinato-N, $C^{3'}$) (acetyl acetonate) [Pt(bzq)(acac)]. 100 mg of Pt(bzq)($\mu$Cl)$_2$Pt(bzq) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright yellow solid (27% yield). $^1$H NMR (360 MHz, acetone-d$_6$), ppm: 9.13 (d, 1H, J 5.4 Hz), 8.25 (d, 1H, J 8.3 Hz), 7.75 (m, 2H), 7.50–7.57 (m, 3H), 7.44 (dd, 1H, J 5.4, 5.4 Hz), 5.52 (s, 1H), 2.04 (s, 6H). See FIG. 4, compound number 2. See also FIG. 1(c).

Platinum (II) (2-benzylpyrinato-N,C2') (acetyl acetonate) [Pt(bzpy)(acac)]. 100 mg of Pt(bzpy)($\mu$-Cl)$_2$Pt(bzpy) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright yellowish green solid (20% yield). $^1$H NMR (500 MHz, CDCl$_3$), ppm: 8.88 (d, 1H), 7.71 (t, 1H), 7.35–7.43 (m, 2H), 7.13 (t, 1H), 6.98–7.02 (m, 2H), 6.91 (t, 1H), 5.49 (s, 1H), 4.16 (s, 2H), 1.96 (s, 3H), 1.95 (s, 3H).

Platinum(II) (2-(2'-thienyl)pyridinato-N, $C^{3'}$) (acetyl acetonate) [Pt(thpy)(acac)]. 100 mg of Pt(thpy)($\mu$Cl)$_2$Pt (thpy) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave bright orange solid (20% yield). $^1$H NMR (500 MHz, CDCl$_3$) ppm: 8.78 (d, 1H), 7.67 (t, 1H), 7.46 (d, 1H), 7.26 (d, 1H), 7.17 (d, 1H), 6.86 (t, 1H), 5.46 (s, 1H), 1.98 (s, 3H), 1.95 (s, 3H).

Platinum(II) (2-(2-(4',5'-benzothienyl)pyridinato-N,$C^{3'}$) (acetyl acetonate) [Pt(btp)(acac)]. 100 mg of Pt(btp)($\beta$-Cl)$_2$Pt(btp) dimer, 25 mg of 2,4-pentanedione and 85 mg of anhydrous sodium carbonate were refluxed at 100° C. in 8 ml of 2-ethoxyethanol under inert gas atmosphere for 15 hours. Cooling to room temperature, addition of cold water and filtration yielded crude product that after drying and flash chromatography (silica/dichloromethane) gave orange-red solid (20% yield). $^1$H NMR (360 MHz, CDCl$_3$), ppm: 8.90 (d, 1H, J 5.9 Hz), 8.75–8.79 (m, 1H), 7.77–7.81 (m, 1H), 7.71 (dt, 1H, J 1.5, 7.8 Hz), 7.27–7.34 (m, 3H), 6.95 (dt, 1H, J 1.5, 6.8 Hz), 5.54 (s, 1H), 2.08 (s, 3H), 2.01 (s, 3H). See FIG. 4, compound number 3. See also FIG. 1(e).

Platinum(II) (2-(4',6'-difluorophenyl)pyridinato-N,$C^{2'}$) (acetyl acetonate) [Pt(4,6-F$_2$ppy)(acac)]. 131 mg of Pt(4,6-F$_2$ ppy)($\mu$-Cl)$_2$Pt(4,6-F$_2$ ppy) dimer, 43 mg of 2,4pentanedione and 109 mg of anhydrous sodium carbonate were refluxed at 100° C. in 10 ml of 2-ethoxyethanol under inert gas atmosphere for 15 hours. Cooling to room temperature, addition of cold water and filtration yielded crude product that after drying and flash chromatography (silica/dichloromethane) gave bright yellow solid. $^1$H NMR (360 MHz, acetone-d$_6$, ppm: 9.06 (dt, 1H, J 1.0, 5.9 Hz), 8.08–8.13 (m, 1H), 8.01 (dt, 1H, J 1.5, 8.3 Hz), 7.38–7.43 (m, 1H), 7.05 (dd, 1H, J 2.4, 9.3 Hz), 6.69–6.76 (m, 1H), 5.61 (s, 1H), 2.01 (s, 3H), 1.99 (s, 3H). See FIG. 4, compound number 4. See also FIG. 1(d).

Platinum (II) (2-(4',5'-difluorophenyl)pyridinato-N, C²') (acetyl acetonate) [Pt(4,5-F₂ppy)(acac)]. 68 mg of Pt(4,5-F₂ppy)(μ-Cl)₂Pt(4,5-F₂ ppy) dimer, 36 mg of 2-picolinoc acid and 57 mg of anhydrous sodium carbonate were refluxed at 100° C. in 5 ml of 2-ethoxyethanol under inert gas atmosphere for 15 hours. Cooling to room temperature, addition of cold water and filtration yielded crude product that after drying and flash chromatography (silica/dichloromethane) gave bright yellow solid. ¹H NMR (360 MHz, acetone-d₆), ppm: 8.99 (d, 1H, J 5.7 Hz), 8.06 (dt, 1H, J 2.3, 8.0 Hz), 7.90 (d, 1H, J 8.0 Hz), 7.62–7.68 (m, 1H), 7.37 (tt, 1H, J 1.7, 5.7 Hz), 7.20–7.25 (m, 1H), 5.58 (s, 1H), 1.99 (s, 3H), 1.98 (s, 3H). See FIG. 4, compound number 6. See also FIG. 1(f).

Platinum(II) (2-(4,5'-difluorophenyl)pyridinato-N, C²') (2-picolinato) [Pt(4,5-F₂ppy)(pico)]. 69 mg of Pt(4,5-F₂ ppy)(μ-Cl)₂Pt(4,5-F₂ ppy) dimer, 30 mg of 2-picolinoc acid and 52 mg of anhydrous sodium carbonate were refluxed at 100° C. in 5 ml of 2-ethoxyethanol under inert gas atmosphere for 15 hours. Cooling to room temperature, addition of cold water and filtration yielded crude product that after drying and flash chromatography (silica/dichloromethane) gave bright yellow solid. ¹H NMR (500 MHz, CDCl₃), ppm: 9.15 (d, 1H, J 5.6 Hz), 9.05 (d, 1H, J 5.6 Hz), 8.08–8.21 (m, 2H), 7.89 (td, 1H, J 1.2, 8.0 Hz), 7.68–7.71 (m, 1H), 7.54 (d, 1H, J 8.0 Hz), 7.32–7.36 (m,1H), 7.12–7.20 (m, 2H). See FIG. 4, compound number 7. See also FIG. 1(g).

Platinum(II) (2-(4'-cyanophenyl)pyridinato-N, C²') (acetyl acetonate) [Pt(cppy)(acac)] 69 mg of Pt(cppy)μ-Cl)₂Pt(cfppy) dimer, 58 mg of 2-picolinoc acid and 52 mg of anhydrous sodium carbonate were refluxed at 100° C. in 5 ml of 2-ethoxyethanol under inert gas atmosphere for 15 hours. Cooling to room temperature, addition of cold water and filtration yielded crude product that after drying and flash chromatography (silica/dichloromethane) gave bright yellow solid. ¹H NMR (360 MHz, acetone-d₆), ppm: 9.07 (dt, 1H, J 1.0, 5.9 Hz), 8.14 (dt, 1H, J 1.5, 7.8 Hz), 8.05 (dt, 1H, J 1.0, 8.3 Hz), 7.77–7.79 (m, 2H), 7.46–7.50 (m, 1H), 7.43 (dd, 1H, J 1.5, 8.3 Hz), 5.61 (s, 1H), 2.01 (s, 6H).

OLED preparation and testing. Polymer blend OLEDs were spun coat from chloroform solution on patterned pre-cleaned and oxygen plasma treated indium tin oxide (ITO) coated glass substrates and covered with vacuum-deposited aluminum(III) tris(8-hydroxyquinolinate) and/or Mg:Ag (10:1 weight ratio) cathode (500 Å) for the single-layer and heterostructure architectures, respectively. Typically, 7.5 ml of a chloroform solution contained 100 mg of PVK, 40 mg of PBD and 2.5 mg of (45F₂ ppy)Pt(acac). Chosen spin-coating conditions (3000 RPM, 40 s, Specialty Coating Systems, Inc.) led to 1300±20 Å-thick PVK:PBD::dye films as determined by ellipsometry (Rudolph automatic ellipsometer equipped with a He:Ne laser). Prior to spinning, the solutions were filtered through a 0.2 μm filter. Tris(8-hydroxyquinoline) aluminum (III) (Sigma-Aldrich, Inc) (Alq₃) was sublimed prior to use. All measurements on the devices were carried out in air at room temperature. Device current-voltage and light intensity characteristics were measured using the LabVIEW™ program by National Instruments with a Keithley 2400 SourceMeter/2000 Multimeter coupled to a Newport 1835-C Optical Meter. Electroluminescence spectra were recorded at room temperature on a PTI QuantaMaster™ Model C-60SE spectrofluorometer.

Other methods known to those skilled in the art of fabricating OLEDs may be used.

While the invention has been described in detail with reference to certain embodiments, it will be recognized by those skilled in the art that there are other embodiments of the invention within the spirit and scope of the claims.

What is claimed is:

1. An organic light emitting device including an emissive layer comprising an organometallic compound, wherein the organometallic compound has a chemical structure represented by a formula selected from the group consisting of:

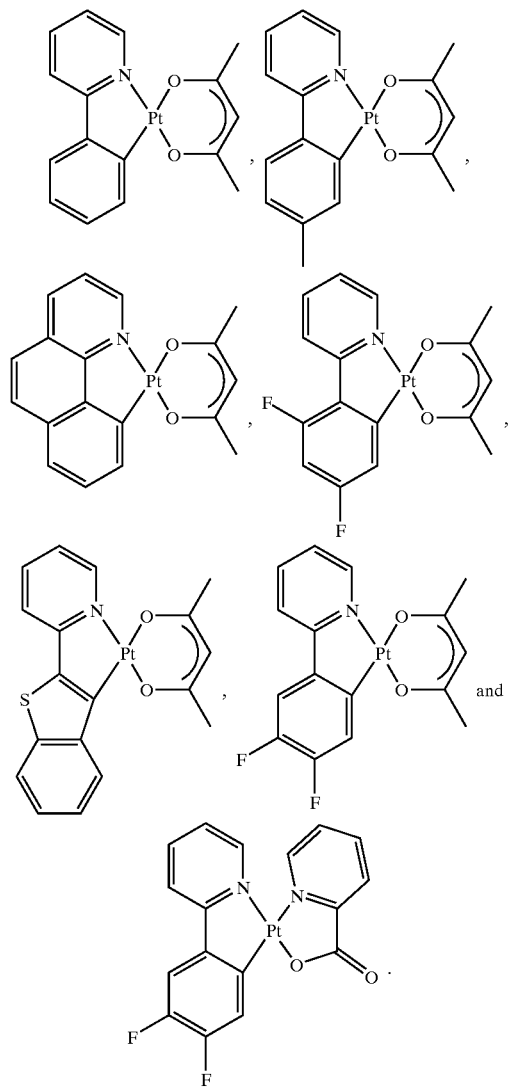

2. An organometallic compound having a chemical structure represented by a formula selected from the group consisting of:

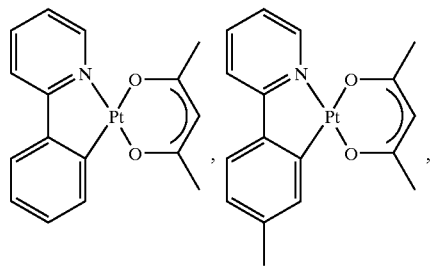

-continued

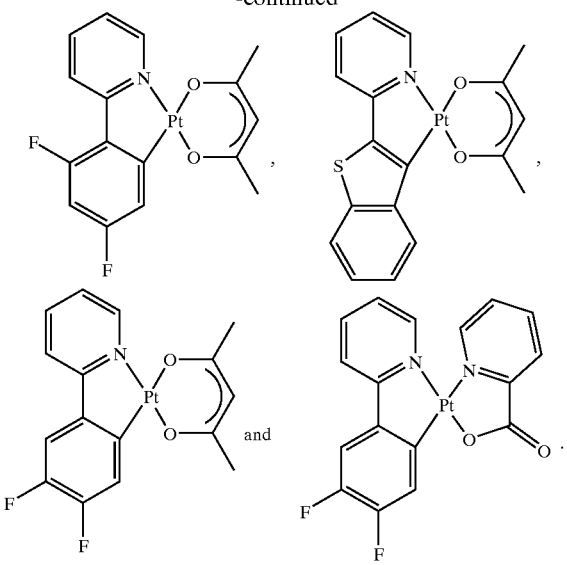

3. The organic light emitting device of claim 1, wherein the organometallic compound has a chemical structure represented by the formula:

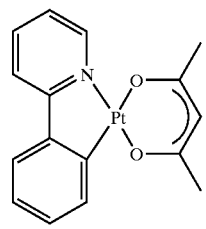

4. The organic light emitting device of claim 1, wherein the organometallic compound has a chemical structure represented by the formula:

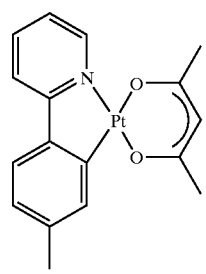

5. The organic light emitting device of claim 1, wherein the organometallic compound has a chemical structure represented by the formula:

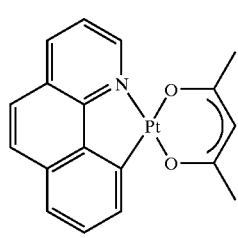

6. The organic light emitting device of claim 1, wherein the organometallic compound has a chemical structure represented by the formula:

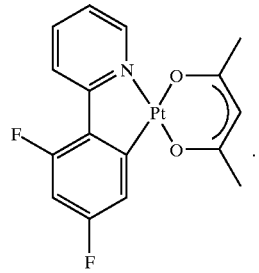

7. The organic light emitting device of claim 1, wherein the organometallic compound has a chemical structure represented by the formula:

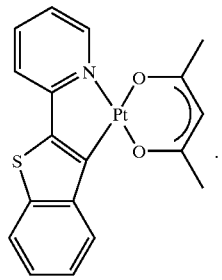

8. The organic light emitting device of claim 1, wherein the organometallic compound has a chemical structure represented by the formula:

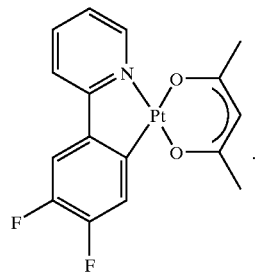

9. The organic light emitting device of claim 1, wherein the organometallic compound has a chemical structure represented by the formula:

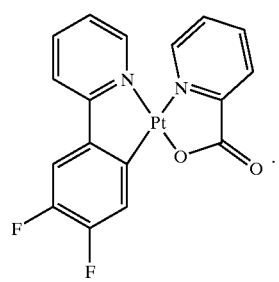

10. The organometallic compound of claim 2, wherein the organometallic compound has a chemical structure represented by the formula:

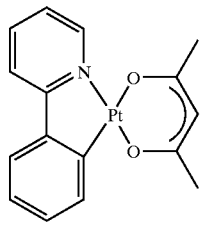

11. The organometallic compound of claim 2, wherein the organometallic compound has a chemical structure represented by the formula:

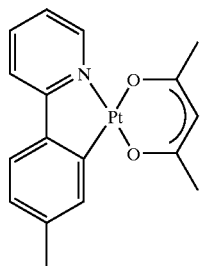

12. The organometallic compound of claim 2, wherein the organometallic compound has a chemical structure represented by the formula:

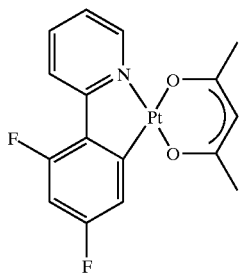

13. The organometallic compound of claim 2, wherein the organometallic compound has a chemical structure represented by the formula:

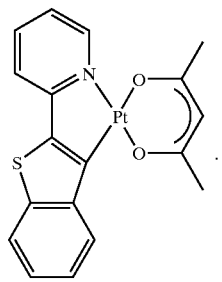

14. The organometallic compound of claim 2, wherein the organometallic compound has a chemical structure represented by the formula:

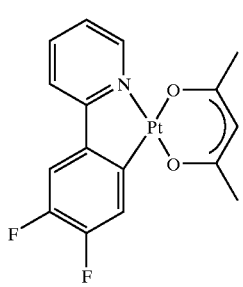

15. The organometallic compound of claim 2, wherein the organometallic compound has a chemical structure represented by the formula:

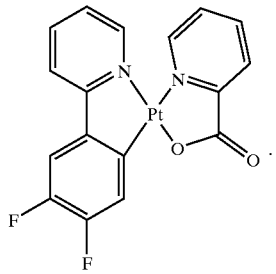

* * * * *